US008439029B2

(12) United States Patent
Helie et al.

(10) Patent No.: US 8,439,029 B2
(45) Date of Patent: May 14, 2013

(54) DEVICE FOR DISPENSING A FLUID PRODUCT

(75) Inventors: Arnaud Helie, La Saussaye (FR); Francois Le Maner, La Vallee Montaure (FR)

(73) Assignee: Aptar France SAS, Le Neubourg (FR)

( * ) Notice: Subject to any disclaimer, the term of this patent is extended or adjusted under 35 U.S.C. 154(b) by 361 days.

(21) Appl. No.: 12/991,845

(22) PCT Filed: May 12, 2009

(86) PCT No.: PCT/FR2009/050871
§ 371 (c)(1), (2), (4) Date: Nov. 23, 2010

(87) PCT Pub. No.: WO2009/147350
PCT Pub. Date: Dec. 10, 2009

(65) Prior Publication Data

US 2011/0088689 A1 Apr. 21, 2011

(30) Foreign Application Priority Data

May 13, 2008 (FR) ..................................... 08 53077

(51) Int. Cl.
*B05B 3/02* (2006.01)
*A61M 11/00* (2006.01)

(52) U.S. Cl.
USPC ................................. 128/200.17; 128/200.23

(58) Field of Classification Search ............. 128/200.17, 128/200.22, 200.23, 200.14, 200.21, 203.19, 128/203.21
See application file for complete search history.

(56) References Cited

U.S. PATENT DOCUMENTS

| | | | | |
|---|---|---|---|---|
| 4,684,043 | A | 8/1987 | Foster et al. | |
| 5,408,994 | A * | 4/1995 | Wass et al. | 128/203.15 |
| 5,465,873 | A | 11/1995 | Mejean et al. | |
| 5,482,187 | A | 1/1996 | Poulsen et al. | |
| 6,510,847 | B1 | 1/2003 | Helgesson et al. | |
| 6,644,305 | B2 * | 11/2003 | MacRae et al. | 128/200.21 |
| 2008/0196718 | A1 * | 8/2008 | Connell et al. | 128/203.15 |
| 2011/0062188 | A1 * | 3/2011 | Lemaner | 222/162 |

FOREIGN PATENT DOCUMENTS

| | | |
|---|---|---|
| FR | 686 891 A | 7/1930 |

* cited by examiner

*Primary Examiner* — Kristen Matter
*Assistant Examiner* — Nyca T Nguyen
(74) *Attorney, Agent, or Firm* — Sughrue Mion, PLLC

(57) ABSTRACT

A fluid dispenser device including a body (10); a reservoir (20) containing fluid; a dispenser member (30), such as a pump or a valve, for dispensing the fluid contained in the reservoir (20) through a dispenser orifice (45); and a cap (50) that is adapted to cover said dispenser orifice (45) in a closed position. The cap (50) is pivotally mounted on the body (10) to turn about an axis (A) between the closed position and an actuation position, the cap (50) including an actuator mechanism (55; 56, 57) adapted to actuate the dispenser member (30) directly, while the cap (50) is turning towards its actuation position.

15 Claims, 3 Drawing Sheets

DEVICE FOR DISPENSING A FLUID PRODUCT

FIELD OF INVENTION

The present invention relates to a fluid dispenser device, and more particularly to a nasal-spray device for a pharmaceutical.

BACKGROUND

Fluid dispenser devices are well known in the state of the art. They generally include a reservoir containing the fluid, on which reservoir there is assembled a dispenser member, e.g. a pump or a valve, that is generally actuated by means of a dispenser head for selectively dispensing the fluid contained inside said reservoir. The dispenser head includes a dispenser orifice through which the fluid is sprayed, e.g. into the user's nose for a nasal-spray device. Numerous devices of this type are actuated manually by the user by moving the reservoir and the dispenser head axially against each other, thereby actuating the dispenser member. However, this type of device presents drawbacks, in particular when the device is of the nasal-spray type, since the axial force exerted by the user in order to actuate the device leads to a risk of the dispenser head moving inside the user's nostril, with risks of injury and/or of the fluid not being dispensed completely or properly on actuation. In order to remedy this problem, lateral actuator devices have been proposed, generally including a lever that is pivotally-mounted on a body and having an inner portion that is adapted to co-operate with one of the dispenser head and the reservoir so as to move said element against the other, and thus actuate the dispenser member. However, such devices are generally quite complex and include a large number of component parts, thereby making manufacture and assembly relatively costly.

Another drawback of fluid dispenser devices relates to the use of a protective cap that the user removes before the device is used. If, after using the device, the user forgets to put the cap back into place, the dispenser orifice risks becoming soiled and/or blocked, consequently preventing the device from being reused as a result of the quality of the fluid being spoilt for the next use. In order to remedy this problem, it has been proposed to make "non-losable" caps that, in any position of the device, remain fastened to the body of the device, and that are thus movable relative to said body between a closed position, in which they close the dispenser orifice, and a working position, in which they uncover it. However, such devices are often quite complex to make, in particular when they are associated with lateral actuator systems, thereby making their manufacture and their assembly relatively costly.

CERTAIN OBJECTS AND ADVANTAGES OF THE INVENTION

An object of the present invention is to provide a fluid dispenser device that does not have the above-mentioned drawbacks.

More particularly, an object of the present invention is to provide a fluid dispenser device that is simple and inexpensive to manufacture and to assemble.

Another object of the present invention is to provide a fluid dispenser device, in particular a nasal-spray device, that guarantees safe and reliable actuation of the device on each actuation, without risk of injury to the user, and that also guarantees closure of the dispenser orifice before and after each use.

BRIEF DESCRIPTION OF THE DRAWINGS

These characteristics and advantages and others of the present invention appear more clearly from the following detailed description, given by way of non-limiting example, and with reference to the accompanying drawings, in which.

DETAILED DESCRIPTION OF CERTAIN NON-LIMITING EMBODIMENTS

Figures 1, 2, 3:
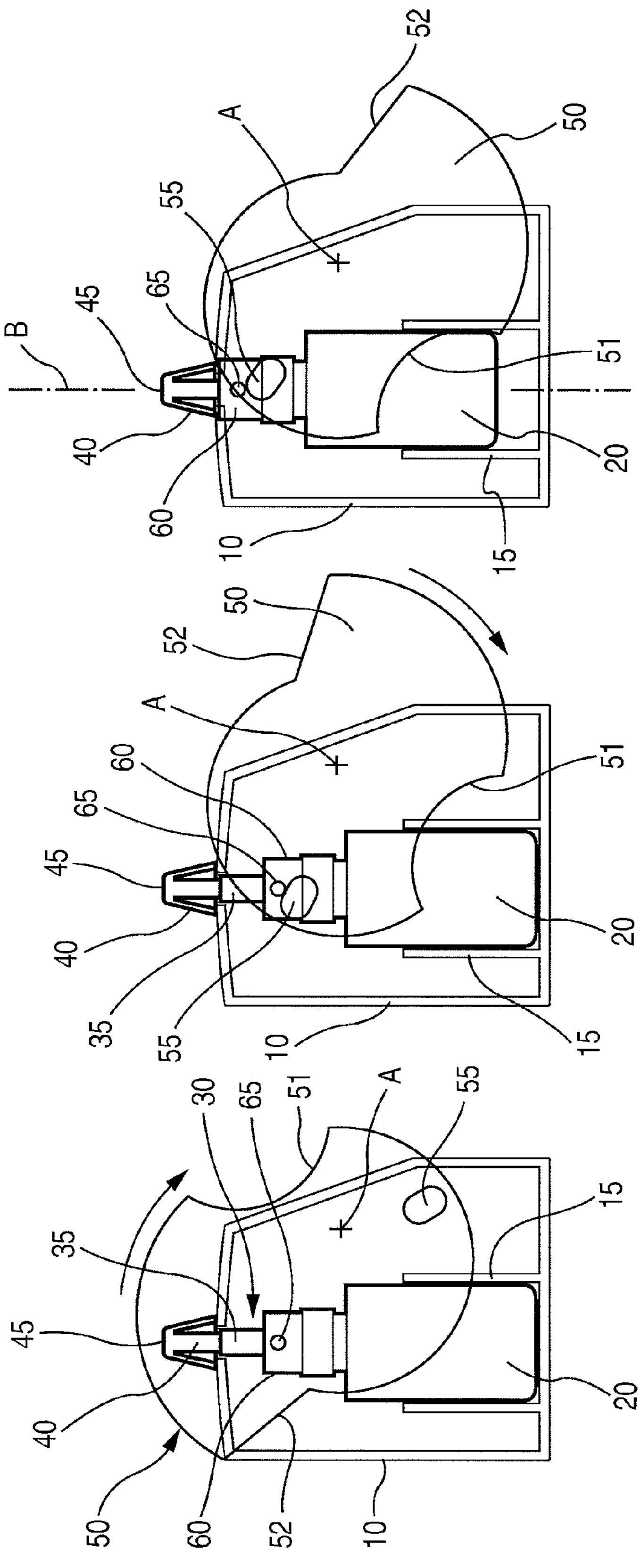
FIGS. 1 to 3 are diagrammatic views of an embodiment, respectively in a rest position, in an intermediate position, and in an actuation position.

With reference to FIGS. 1 to 3, which show an embodiment, the fluid dispenser device includes a body 10 in which there is assembled a reservoir 20 that contains fluid, in particular a pharmaceutical for spraying into the user's nose. A dispenser member 30, such as a pump or a valve, is assembled on said reservoir 20, advantageously by means of a fastener ring 60. The dispenser member comprises a dispenser-member body, such as a pump body or a valve body (not shown in the drawings for the purpose of clarity), and a dispenser element 35, such as a piston rod or a valve member, that is slidably mounted in said dispenser-member body. In conventional manner, the dispenser element 35 is driven into the dispenser-member body so as to actuate said dispenser member 30. Advantageously, a dispenser head 40 is assembled on said dispenser member 30, said dispenser head 40 incorporating a dispenser orifice 45 through which the fluid is dispensed. For certain particular pumps, it should be noted that the dispenser head 40 may form the body of the dispenser member 30, this type of pusher-pump being entirely usable with the present invention.

In the invention, a cap 50 is pivotally mounted on the body 10 to turn between a closed position in which it covers the dispenser orifice 45, advantageously in leaktight manner, and an actuation position. Advantageously, the cap 50 is fastened in irremovable manner to the body 10, and turns about an axis of rotation A, as shown in the figures. Advantageously, the cap includes one or more bearing zones 51, 52 against which the user presses so as to actuate the device. In the embodiment in FIGS. 1 to 3, the cap includes a first bearing zone 51 against which the user presses so as to move the cap 50 from its rest position shown in FIG. 1 towards an intermediate position shown in FIG. 2, and a second bearing zone 52 against which the user presses so as to actuate the device.

In the invention, the cap 50 includes actuator means 55 that are adapted, when the cap 50 has been turned to its actuation position, to actuate said dispenser member 30 directly. The actuator means are adapted to co-operate with a portion 65 that is secured to the reservoir 20, to the dispenser member 30, and/or to any element that is secured thereto, e.g. the fastener ring 60 that serves to fasten the dispenser member 30 onto the reservoir 20. The term "actuate . . . directly" means that the actuator means 55 of the cap co-operate directly with the portion 65, without having to provide an intermediate part. This makes it possible to limit the number of component parts, and thus reduce the cost of manufacture and of assembly. In the embodiment shown in FIGS. 1 to 3, the actuator means may be formed by a lug 55 that projects inside said cap 50.

As shown in the figures, the cap includes an intermediate position, shown in particular in FIG. 2, in which the dispenser orifice 45 is uncovered, but the dispenser member 30 is not yet actuated. After moving the cap 50 from its rest position towards the intermediate position, the user may then place the dispenser head 40 in a nostril, then continue to turn the cap 50 towards its actuation position, thereby actuating the dispenser member 30 and dispensing the dose of fluid into the nose.

As shown in FIGS. 2 and 3, the direction in which the user exerts actuation force on the bearing zone 52 of the cap 50 is different from the longitudinal axis of symmetry B of the device, which longitudinal axis of symmetry corresponds to the direction in which the dispenser element 35 moves when the dispenser member 30 is actuated. The cap 50 thus provides a kind of lateral actuator system that makes it possible to avoid any risk of injuring the user when the device is actuated. Advantageously, the portion 65 against which the actuator means 55 of the cap 50 co-operate, is formed by a projection 65 that is secured to a ring. The ring is preferably the fastener ring 60 that serves to fasten the dispenser member 30 onto the reservoir 20, but it could also be a fitted ring that is fastened around the fastener ring. Naturally, if the projection 65 is integral with the fastener ring itself, the invention makes it possible to reduce the number of parts by one more, thereby reducing the cost of manufacture and of assembly of the device. In a variant, the projection 65 could also be integral with the reservoir 20 or with the body of the dispenser member 30.

Advantageously, as shown in the figures, the actuator means 55 act actively on the projection 65 when the cap 50 is in its intermediate position. Consequently, as the user continues to turn the cap 50 from its intermediate position towards its actuation position, the actuator means 55 move the projection 65, and thus actuate the dispenser member. Preferably, the actuator means 55 have a rounded shape, and the projection 65 also preferably has a rounded shape, thereby guaranteeing sliding that is regular, without them bumping against each other while the device is being actuated.

In the embodiment shown in FIGS. 1 to 3, the dispenser head 40 is stationary relative to the body 10, and it is thus the reservoir and the dispenser member 30 that move relative to the body during actuation. Preferably, the body 10 may include reservoir guide means 15 that are adapted to guide the reservoir 20 when said reservoir moves along its longitudinal axis of symmetry B.

Figure 6:
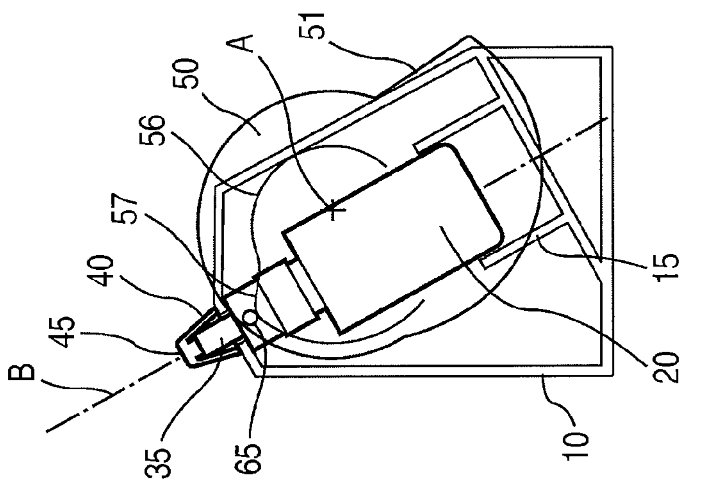
FIGS. 4 to 6 are diagrammatic views of an embodiment of the present invention, respectively in the rest position, in the intermediate position, and in the actuation position.
Figure 5:
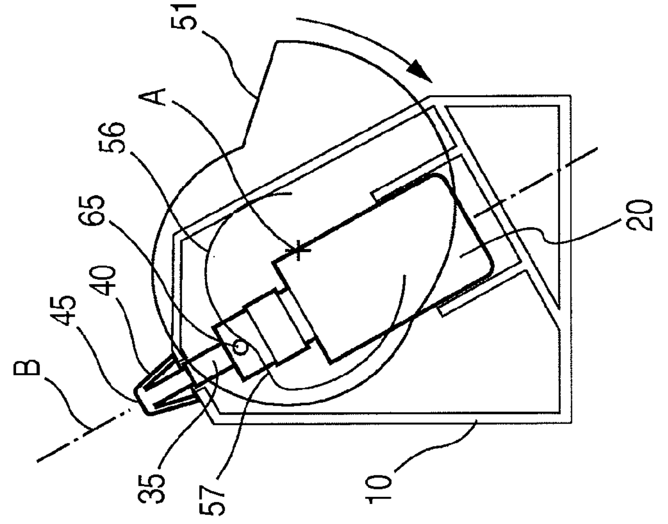
Figure 4:
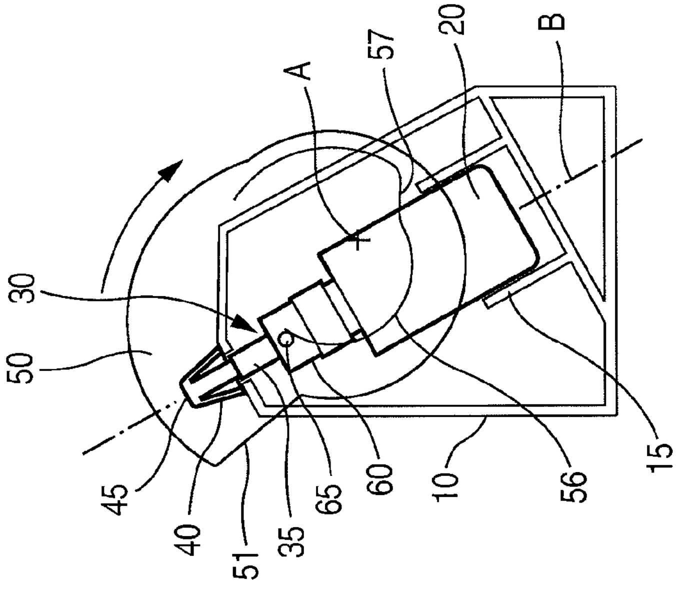

FIGS. 4 to 6 show an embodiment of the present invention. The main difference in this embodiment compared to the embodiment in FIGS. 1 to 3 relates to the actuator means of the cap 50, that, in this embodiment, are formed by a cam surface 56, 57 replacing the lug 55 in FIGS. 1 to 3. In addition, as can clearly be seen in the figures, the longitudinal axis of symmetry B of the reservoir and of the dispenser member 30 slopes relative to the body 10 when said body is in its upright position shown in FIGS. 4 to 6.

Naturally, such a sloping position could also be provided in the embodiment described above.

In addition, the cam surface cap 50 of this embodiment could be used with a device that does not slope relative to the body.

With reference more precisely to FIGS. 4 to 6, the cam surface of the cap 50 includes a first profile 56, preferably a substantially cylindrical profile, that slides against the projection 65 without moving it while the cap 50 is moving from its rest position, shown in FIG. 4, towards its intermediate position, shown in FIG. 5. Starting from the intermediate position, the cam surface includes a second profile 57, preferably a substantially rectilinear profile, that then co-operates with said projection 65 so as to move and thus actuate the dispenser member 30, while the cap 50 is turning from its intermediate position, shown in FIG. 5, towards its actuation position, shown in FIG. 6. In this second embodiment, the dispenser head 40 is also stationary relative to the body 10, and it is still the reservoir 20 and the dispenser member 30 that move against said head 40, inside said body 10, during actuation.

Figure 9:
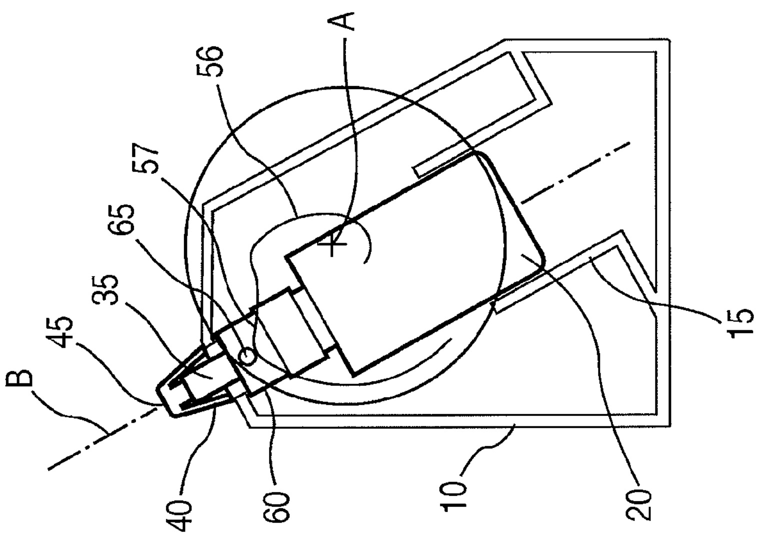
FIGS. 7 to 9 are diagrammatic views of another embodiment of the present invention, respectively in the rest position, in the intermediate position, and in the actuation position.
Figure 8:
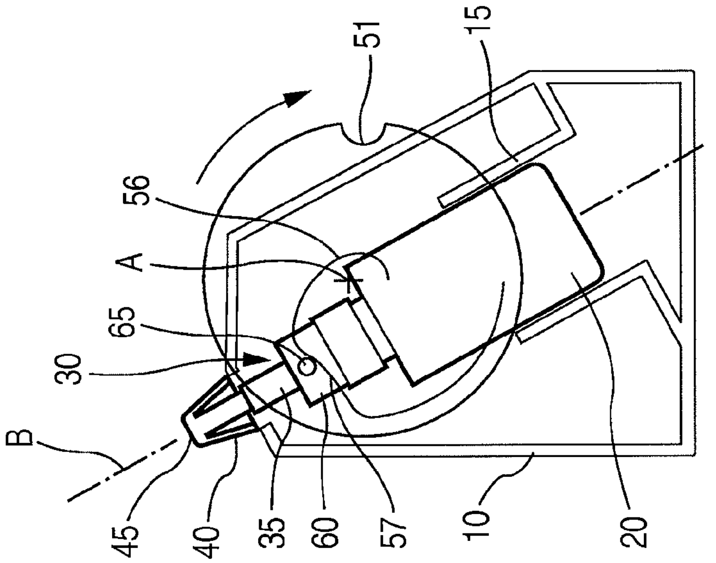
Figure 7:
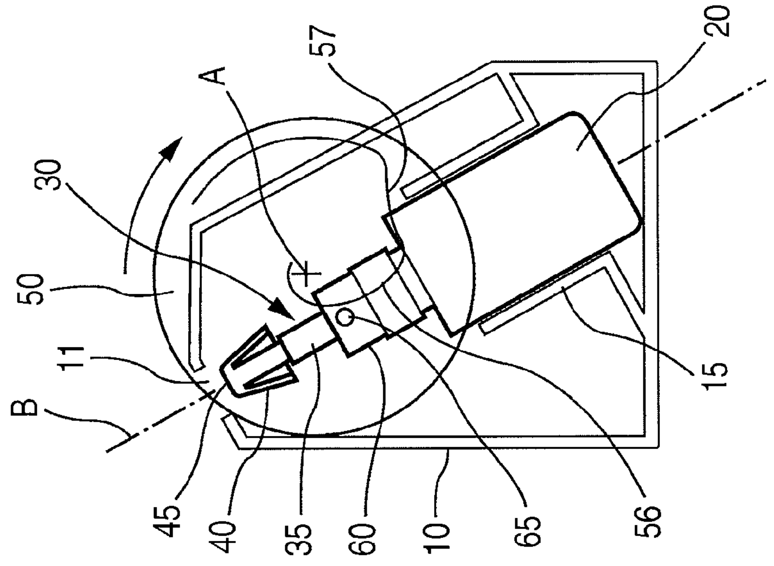

FIGS. 7 to 9 show another embodiment of the invention. This other embodiment is similar to the embodiment of FIGS. 4 to 6 in that the device slopes relative to the body 10, and in that the cap 50 includes a cam surface for actuating the device. However, in this other embodiment, the dispenser head 40 is not stationary relative to the body 10, but moves relative to said body between a rest position in which it is retracted inside the body 10, as shown in FIG. 7, and a dispensing position in which the dispenser head 40 extends out from the body 10, as shown both in FIG. 8 that shows the intermediate position, and in FIG. 9 that shows the actuation position. In this other embodiment, while the cap 50 is moving from its rest position towards its intermediate position, the unit formed by the reservoir 20, the dispenser member 30, and the dispenser head 40 thus moves as a single unit between a retracted position and an extended position, without the dispenser member 30 being actuated. When the device arrives in the intermediate position, continued turning of the cap 50 about its axis of rotation A thus causes the projection 65 to move relative to the dispenser head 40, and thus causes the dispenser member 30 to be actuated. To do this, the cap 50 advantageously includes a cam surface that is provided with a first profile 56 that co-operates with the projection 65 so as to move the device as a single unit, without the dispenser member 30 being actuated, and a second profile 57 that causes the projection 65 to move relative to the dispenser head 40.

Thus, in the two embodiments shown in FIGS. 4 to 6 and in FIGS. 7 to 9 respectively, the cam surface 56, 57 comprises a first profile 56 that co-operates with said projection 65, without said dispenser member 30 being moved relative to said dispenser head 40, while the cap 50 is turning from the rest position towards the intermediate position, and a second profile 57 that co-operates with said projection 65 so as to move said dispenser member 30 relative to said dispenser head 40, and thus actuate the dispenser member 30, while the cap 50 is turning from the intermediate position towards the actuation position.

Advantageously, abutment means (not shown) are provided in the intermediate position so as to block any additional axial movement of the dispenser head 40 after the intermediate position has been reached, and thus cause the dispenser member 30 to be actuated, while the cap 50 is moving from the intermediate position towards the actuation position.

In a variant, it should be noted that the cap 50 could include secondary means that are adapted to move the unit formed by the reservoir 20, the dispenser member 30, and the dispenser head 40 from the retracted position towards the extended intermediate position. The secondary means could be completely independent from the cam surface, and, by way of example, could co-operate with another portion of the unit so as to achieve this first movement. Then, while the cap 50 is turning from the intermediate position towards the actuation position, a cam surface 57 of appropriate shape and profile would co-operate with the projection 65 so as to actuate the dispenser member 30.

Once again, naturally this third embodiment could also be provided with a device that does not slope relative to the body 10, and with one or the other of the actuator systems of the cap described in the above-described embodiments.

In general, the various characteristics shown in the three embodiments could be combined together in any desired and appropriate manner, and any useful modification could be applied by a person skilled in the art to the three above-described embodiments, that are given merely by way of non-limiting example, without going beyond the ambit of the present invention as defined by the accompanying claims.

The invention claimed is:

1. A fluid dispenser device comprising: a body; a reservoir containing fluid; a dispenser member for dispensing the fluid contained in said reservoir through a dispenser orifice; and a cap that is adapted to cover said dispenser orifice in a closed position; said cap being pivotally mounted on said body to turn about an axis between the closed position and an actuation position, said cap including an actuator mechanism adapted to actuate said dispenser member directly while the cap is turning towards the actuation position, said cap including a cam surface incorporated on an inner surface of the cap, that is adapted to co-operate with a projection that is secured to at least one of said reservoir, to said dispenser member, and to an element that is secured to said dispenser member, said cap including an intermediate position in which said cap uncovers the dispenser orifice, without said dispenser member being actuated, continued turning of the cap from the intermediate position towards the actuation position causing said dispenser member to be actuated, said cam surface comprises a first profile that co-operates with said projection, without said dispenser member being moved relative to said dispenser head while the cap is turning from the rest position towards the intermediate position, and a second profile that co-operates with said projection so as to move said dispenser member relative to said dispenser head, and thus actuate the dispenser member, while the cap is turning from the intermediate position towards the actuation position;

wherein said first profile is substantially cylindrical and slides against said projection and said second profile is substantially rectilinear.

2. A device according to claim 1, wherein said first profile (56) slides against said projection (65) without moving said projection while the cap is turning from the rest position towards the intermediate position, said second profile co-operating with said projection so as to move said projection and thus actuate the dispenser member while the cap is turning from the intermediate position towards the actuation position.

3. A device according to claim 1, wherein said first profile co-operates with said projection so as to move the reservoir, the dispenser member, and the dispenser head as a single unit relative to the body while the cap is turning from the rest position towards the intermediate position.

4. A device according to claim 1, wherein the dispenser member comprises a dispenser-member body and a dispenser element that is movable in said dispenser-member body between a rest position and a dispensing position, said actuator mechanism of said cap being adapted to move said dispenser element towards the dispensing position while the cap is moving towards its the actuation position.

5. A device according to claim 1, wherein the dispenser orifice is formed in a dispenser head that is stationary relative to said body, said cap moving the reservoir and the dispenser member against said stationary dispenser head, thereby actuating the dispenser member.

6. A device according to claim 1, wherein the dispenser orifice is formed in a dispenser head that is movable relative to said body between a rest position in which the dispenser head is retracted inside the body and a dispensing position in which the dispenser head extends out from the body.

7. A device according to claim 1, wherein the reservoir is movable in translation along its longitudinal axis of symmetry, the body including a guide for guiding said reservoir.

8. A device according to claim 7, wherein said longitudinal axis slopes relative to the body of the device.

9. A device according to claim 1, wherein said cap co-operates with a portion of a fastener ring that fastens the dispenser member onto the reservoir.

10. A device according to claim 1, wherein said cap co-operates with a portion of a ring that is fastened to the fastener ring that fastens the dispenser member onto the reservoir.

11. A device according to claim 1, wherein said cap includes at least one bearing zone against which the user presses so as to actuate the device.

12. A device according to claim 1, wherein said cap is fastened in irremovable manner on said body.

13. A device according to claim 1, wherein said cap closes said dispenser orifice in leaktight manner, in the rest position.

14. The device according to claim 1, wherein the dispenser member is a pump or a valve.

15. The device according to claim 1, wherein the element secured to said dispenser member is a fastener ring for fastening the dispenser member onto the reservoir.

* * * * *